United States Patent [19]
Engelhardt et al.

[11] Patent Number: 4,877,540
[45] Date of Patent: Oct. 31, 1989

[54] METHYLOLATED AND OPTIONALLY ETHERIFIED URETHANES CONTAINING FLUOROALKYL LIGANDS

[75] Inventors: Fritz Engelhardt; Karl Hintermeier, both of Frankfurt am Main; Manfred Müller, Gelnhausen; Norbert Münch, Kelkheim; Hans Wagener, Hofheim, all of Fed. Rep. of Germany

[73] Assignee: Cassella Aktiengesellschaft, Frankfurt am Main, Fed. Rep. of Germany

[21] Appl. No.: 229,509

[22] Filed: Aug. 8, 1988

[30] Foreign Application Priority Data

Aug. 19, 1987 [DE] Fed. Rep. of Germany ....... 3727665

[51] Int. Cl.$^4$ ................. C07C 125/06; C07C 127/24; C07C 143/74; D06M 15/57

[52] U.S. Cl. .................................. 252/8.75; 8/115.51; 8/115.6; 8/115.64; 8/115.66; 252/8.7; 252/8.8; 252/8.9; 560/19; 560/24; 560/25; 560/26; 560/29; 560/33; 560/34; 560/155; 560/157; 560/158; 560/159; 560/160; 560/165

[58] Field of Search ............... 8/115.51, 115.6, 115.64, 8/115.66; 252/8.75; 560/26, 33, 158, 159, 165

[56] References Cited

U.S. PATENT DOCUMENTS

| | | | |
|---|---|---|---|
| 3,636,085 | 1/1972 | Kleimer | 560/196 |
| 3,824,126 | 7/1974 | Katsushima et al. | 427/394 |
| 3,856,849 | 12/1974 | Emden et al. | 560/220 |
| 4,035,506 | 12/1977 | Lucas et al. | 514/562 |
| 4,264,484 | 4/1981 | Patel | 8/115.6 |
| 4,340,749 | 7/1982 | Patel | 560/182 |
| 4,468,527 | 8/1984 | Patel | 564/96 |

Primary Examiner—A. Lionel Clingman
Attorney, Agent, or Firm—Connolly and Hutz

[57] ABSTRACT

Methylolated and optionally etherified urethanes containing fluoroalkyl ligans with-formaldehyde, with or witout subsequent etherification, and are in the form of their solutions or aqueous dispersions suitable for the treatment of textiles and leather.

15 Claims, No Drawings

METHYLOLATED AND OPTIONALLY ETHERIFIED URETHANES CONTAINING FLUOROALKYL LIGANDS

The invention relates to methylolated and optionally etherified urethanes containing fluoroalkyl ligands, processes for their preparation, their aqueous dispersions and their use.

Urethanes containing fluoroalkyl ligands for the treatment of textiles are already known, compare, for example, U.S. Pat. Nos. 4,264,484, 4,340,749 and 4,468,527. The methylolated and optionally etherified urethanes according to the invention which contain fluoroalkyl ligands are superior to the previously known compounds containing fluoroalkyl ligands.

The methylolated and optionally etherified urethanes according to the invention containing fluoroalkyl ligands can be prepared by reaction of a urethane containing fluoroalkyl ligands, of the general formula 1

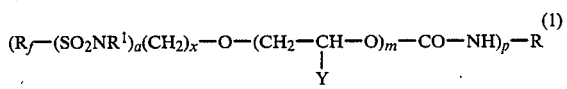

(1)

wherein $R_f$ denotes a perfluoroalkyl group with 4 to 20 C atoms, $R^1$ denotes hydrogen or an alkyl group with 1 to 4 C atoms, a denotes the number 0 or 1, x denotes a number from 1 to 4, Y denotes hydrogen, —CH$_3$ or —CH$_2$Cl, R denotes an organic radical, p denotes a number from 1 to 4 and m denotes a number from 0 to 4, with formaldehyde in a molar ratio of 1 : (0.5 to 1.1 t), t being the total number of methylolatable —NH groups present in the compound, and if appropriate subsequent etherification with a lower alkanol with 1 to 4 C atoms or ethylene glycol monoalkyl ether with 1 to 4 C atoms in the alkyl radical.

The perfluoroalkyl group $R_f$ can be straight-chain or branched; in the case of a branched perfluoroalkyl group, end branching is preferred. Of the two perfluoroalkyl groups, that is to say the straight-chain or branched, the straight-chain groups are preferred. The perfluoroalkyl radical is as a rule a mixture of perfluoroalkyl groups with the abovementioned number of C atoms. The perfluoroalkyl group $R_f$ preferably has 6 to 16 C atoms.

For a, the number zero is preferred. The alkyl radical $R^1$ can be straight-chain or branched. The number 2 is preferred for x.

The organic radical R can be an aliphatic, aromatic or araliphatic radical, which can also contain hetero atoms, above all nitrogen and/or oxygen, and in particular one or more methylolatable —NH groups.

Examples of divalent aliphatic radicals R are those of the formulae 2, 3 and 4

wherein q represents a number from 2 to 10, in particular 2 to 8.

Examples of divalent aromatic radicals R are phenylene radicals of the formula 5, in particular 1,3- and 1,4-phenylene radicals of the formulae 5a and 5b, which can be substituted in the nucleus, above all by alkyl radicals, in particular methyl:

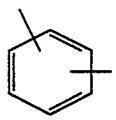

(5)

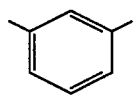

(5a)

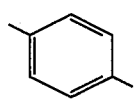

(5b)

A divalent araliphatic radical R can also be a radical of the formula 6

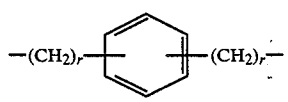

(6)

wherein r denotes a number from 1 to 6 and the phenyl nucleus can also be substituted, above all by alkyl radicals, in particular by methyl.

Other organic radicals R are those of the following formulae 7 to 12

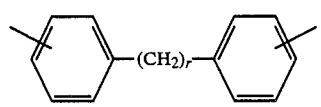

(7)

in particular

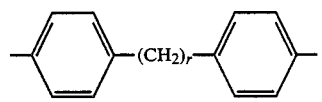

(7a)

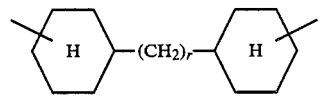

(8)

in particular

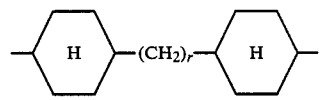

(8a)

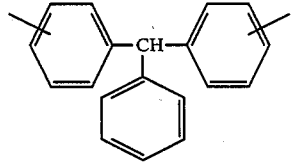

(9)

in particular

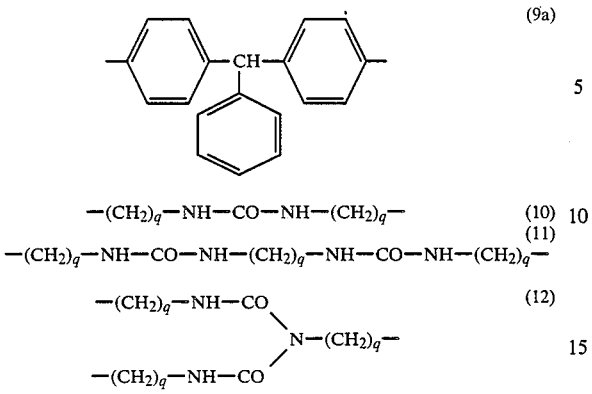 (9a)

$-(CH_2)_q-NH-CO-NH-(CH_2)_q-$ (10)

$-(CH_2)_q-NH-CO-NH-(CH_2)_q-NH-CO-NH-(CH_2)_q-$ (11)

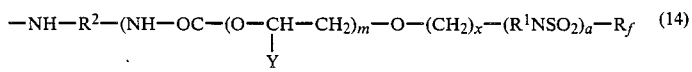 (12)

wherein, in the formulae 7, 7a, 8 and 8a, r denotes a number from 1 to 6, preferably 1. In the formulae 10 to 12, q denotes a number from 2 to 10, in particular 2 to 8 and preferably 6.

R can furthermore be a radical of the formula 13

$-R^2-(NH-CO-R^3)_w$ (13)

wherein w denotes a number from 1 to 2, with the proviso that the sum of p+w is not more than 3 and $R^2$ is a (p+w)-valent organic radical, for example one of the aliphatic, aromatic or araliphatic radicals of the formulae 2 to 9 given for R above or a radical of the formulae 10 to 12, and $R^3$ denotes a radical of the formulae 14 to 16

 (14)

$-O-(CH_2CH_2CH_2CH_2O)_sH$ (15)

$-O-(CH_2CH_2OCH_2CH_2O)_sH$ (16)

or the radical of a CH-acid or NH-acid compound, or a radical of the formula 17

$-X^1-R^4$ (17)

In the formulae 15 and 16, s is a number from 1 to 15, preferably 1 to 10.

$R^2$ is preferably a radical of the formula 18

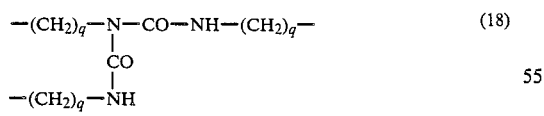 (18)

wherein q denotes a number from 2 to 10, in particular 2 to 8 and preferably 6.

$R^3$ also represents, for example, the radical formed from a CH-acid or NH-acid compound by removal of a hydrogen atom. Such CH-acid compounds are, for example, compounds with an active methylene group, such as, for example, malonic esters, cyanoacetic esters, acetylacetone, acetoacetic esters, succinic acid esters, N-methylpyrrolidone and the like. Suitable NH-acid compounds are, for example, lactams, such as, for example, ε-caprolactam, and pyrrolidone.

In the formula 17, $X^1$ denotes one of the groups corresponding to the following formulae 19 to 23, which can be mono- or polysubstituted, preferably monosubstituted, by an alkyl group with 1 to 4 C atoms (the formulae 19 to 23 represent radicals of aromatic dihydroxy compounds, diamino compounds and aminohydroxy compounds which are optionally substituted by $C_1$- to $C_4$-alkyl groups and are present after release of active hydrogen atoms to isocyanate groups):

 (19)

 (20)

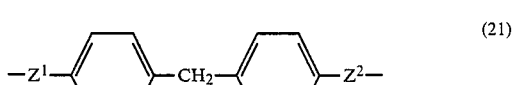 (21)

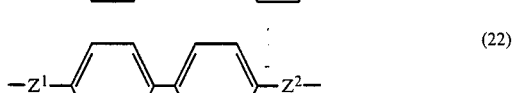 (22)

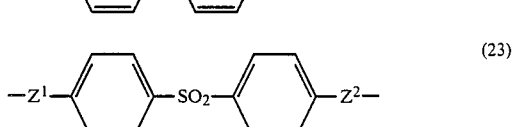 (23)

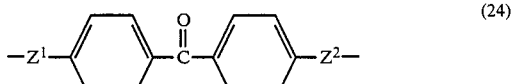 (24)

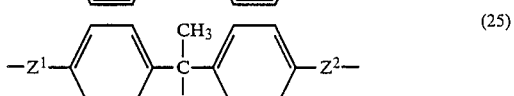 (25)

 (26)

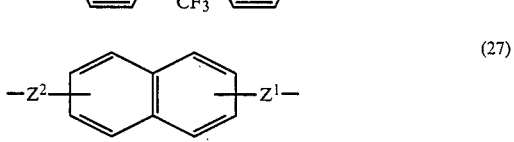 (27)

wherein $Z^1$ and $Z^2$, which can be identical or different, stand for O or NH and $R^4$ denotes the hydrogen atom, an alkyl group with 1 to 4 C atoms or a group corresponding to the following formula 28

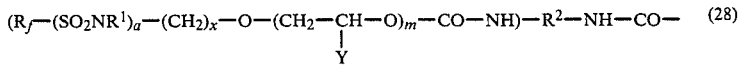 (28)

Preferred radicals R are:

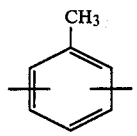 (29)

in particular

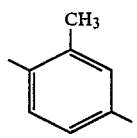 (29a)

and furthermore:

The alkyl radicals present in the compound of the formula 1 can be straight-chain or branched.

Preferred starting compounds of the formula 1 are those which have, for $R_f$, one of the above preferred perfluoroalkyl radicals with 6 to 16 C atoms and in which a denotes O and x denotes 2, and in which R has one of the preferred meanings of the formulae 29 and 29a to 33, wherein, in the formulae 30 to 33, q preferably denotes 6. Y preferably denotes —CH$_2$Cl.

The methylolation according to the invention is carried out so that 1 mol of the compound of the general formula 1 is reacted with 0.5 mol to 1.1 t mol of formaldehyde, t being the total number of methylolatable —NH groups present in the compound of the general formula 1, at a temperature of 20° to 70° C., preferably 30° to 65° C. The methylolation can be carried out without a solvent, in which case paraformaldehyde or

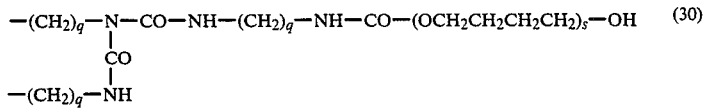 (30)

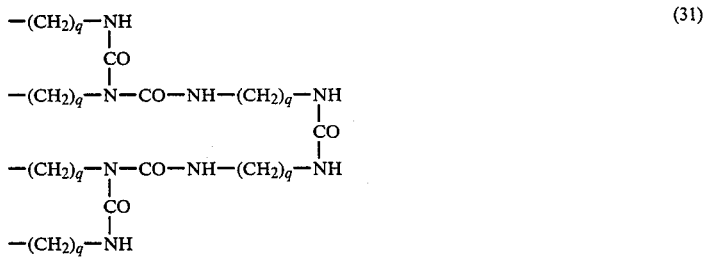 (31)

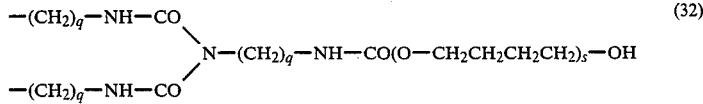 (32)

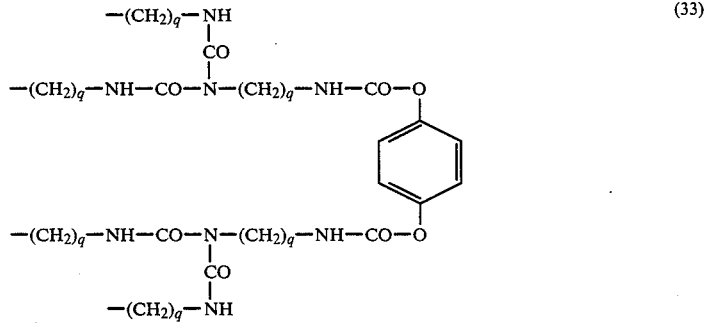 (33)

In the above formulae 30 to 33, q denotes a number from 2 to 10, in particular 2 to 8, preferably 6, and s denotes a number from 1 to 15, in particular 1 to 10, and identical or different radicals of the formula

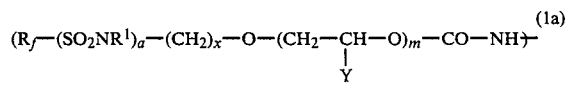 (1a)

are present on the free bonds.

aqueous formaldehyde is reacted with molten starting substance of the general formula 1. However, the methylolation is in general carried out in a solvent. Suitable solvents are polar organic solvents which are inert towards the starting and end compounds, such as, for example, acid amides, such as dimethylformamide; N-methyl-pyrrolidone; esters, such as butyl acetate; glycol ethers, such as ethylene glycol dimethyl ether and diethylene glycol dimethyl ether, and alcohols, such as, in particular, those with 1 to 4 C atoms, such as methanol, butanol and isobutanol.

The formaldehyde can thereby be used in the form of aqueous solutions if these are miscible with the solvent. However, the formaldehyde is advantageously used in the form of a solution in an organic solvent. Suitable solutions are, for example, the commercially available solutions of formaldehyde in isobutanol or solutions of paraformaldehyde in an organic solvent, for example an alkanol.

The molar ratio between the compound of the formula 1 and formaldehyde is chosen, in particular, so that it is 1 : (0.5 to (t−1)), t being the total number of methylolatable —NH groups present in the molecule. The molar ratio of compound of the formula 1 : formaldehyde during the methylolation is preferably 1 : (0.5 to 0.525 t), t having the meaning given. As can be seen from the above, only partial methylolation is preferably carried out.

The methylolation is preferably carried out in the presence of an alkaline catalyst, for which tertiary amines are preferably used, thus, for example, N,N-dimethyl-ethanolamine or triethylenediamine (=1,4-diazabicyclo(2.2.2)-octane=DABCO). In view of subsequent dispersion of the optionally etherified methylolation product, it is advantageous to use as the alkaline catalyst a tertiary amine which acts as an emulsifier during the subsequent dispersion. Examples of suitable amines are tertiary amines containing perfluoroalkyl groups, such as, for example, those shown below:

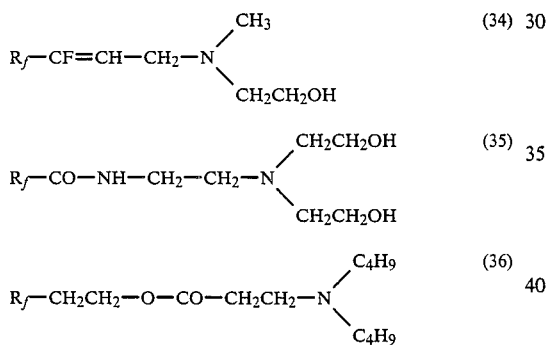

wherein $R_f$ is a perfluoroalkyl radical with 4 to 15 C atoms, preferably 6 to 12 C atoms.

The methylolation is usually carrried out in the presence of 0.01 to 5% by weight, preferably 0.1 to 1% by weight, of a basic catalyst, based on the compound to be methylolated. Instead of a basic catalyst, it is also possible to use a mixture of two or more basic catalysts.

If appropriate, the methylolation can be followed by etherification with a lower alkanol, that is to say an alkanol with 1 to 4 C atoms, or an ethylene glycol monoalkyl ether with 1 to 4 C atoms in the alkyl radical. The alkanol and the alkyl radical in the ethylene glycol monoalkyl ether can be straight-chain or branched. The etherification optionally carried out as a rule takes place so that the etherifying alcohol is added in excess to the methylolation product and the reaction medium is rendered acid, for example by addition of a mineral acid. The mixture is then heated at temperatures of 40° to 65° C. for a few hours, as a rule 1 ½ to 4 hours, and finally excess etherifying alcohol is distilled off under reduced pressure.

The methylolation according to the invention can also advantageously be carried out at the same time as dispersion of the compound of the formula 1 to be methylolated. This dispersion is carried out in the same manner as the dispersion of the methylolated and optionally etherified compounds which is still to be described.

After the methylolation according to the invention and after the optional etherification following the methylolation, all or preferably some of the hydrogen atoms which had originally been present on the methylolatable —NH groups in the compound of the formula 1 are replaced by —CH$_2$OH or —CH$_2$OR$^5$ or —CH$_2$OCH$_2$CH$_2$OR$^5$ groups, wherein R$^5$ denotes straight-chain or branched alkyl with 1 to 4 C atoms. In the methylolated and optionally etherified compounds according to the invention, the ratio between the total number t of methylolatable —NH groups which were originally present and the total number of —N(CH$_2$OH) groups present or of —N(CH$_2$OR$^5$) and/or —N(CH$_2$OCH$_2$CH$_2$OR$^5$) groups present is preferably 1:(0.5 to (t−1)), preferably 1:(0.5 to 0.525 t).

The methylolated and optionally etherified urethanes according to the invention containing fluoroalkyl ligands are superior to the corresponding non-methylolated products containing fluoroalkyl ligands in respect of the finishing effect and resistance to washing in the hydrophobic and oleophobic treatment of textile and of leather.

The compounds according to the invention are outstandingly suitable for the treatment of textiles and of leather and thereby produce, in particular, oleophobic, hydrophobic, dirt repellant and conductivity-improving effects. They can be used in the form of their solutions in organic solvents or in the form of their aqueous dispersions.

Suitable organic solvents for use of the compounds according to the invention from their solutions are, for example: alcohols, such as, for example, isopropanol; ketones, such as, for example, acetone, methyl ethyl ketone, methyl propyl ketone and diethyl ketone; esters, such as, for example, ethyl acetate, propyl acetate and butyl acetate, or mixtures of two or more organic solvents. The active compound content of the organic solution can vary within wide limits and is preferably 1 to 20% by weight. The organic solution can also contain two or more active compounds according to the invention and if appropriate also other finishing agents and/or auxiliaries.

The active compounds according to the invention are preferably used from their aqueous dispersions, and these likewise can preferably contain solvents.

To prepare the aqueous dispersions, the active compounds, together with cationic or anionic and if appropriate non-ionic dispersing and/or emulsifying agents and if appropriate other auxiliaries and solvents, are dispersed in water, a relatively large amount of energy being supplied. Examples of possible dispersing and/or emulsifying agents of this type are compounds of the formulae 34 to 36 and the cationic, anionic and nonionic emulsifying and dispersing agents still to be mentioned. The active compounds are thereby taken in at least part of the amount of solvent or solvent mixture to be used and the dispersion is advantageously divided into two part steps, predispersion being carried out first, followed by fine dispersion. The predispersion also advantageously carried out by using high shearing forces, for example by using a high-speed stirrer, such as, for example, in a dispersing machine of the Ultraturrax type, and the predispersion thereby obtained is then subjected, for example, to ultrasonic treatment or treatment in a high pressure homogenizer. After the end of this treatment, the particle size in the dispersion is equal to or less than 1 μm to the extent of more than 80%, preferably to the extent of more than 95%.

As a rule, the finished aqueous dispersion contains 5 to 30% by weight of active compound according to the invention, 2 to 15% by weight of dispersing and/or emulsifying agent and 5 to 30% by weight of a solvent or solvent mixture, the remainder being water. It is of course also possible to use, in the dispersion, a mixture of active compounds according to the invention instead of one active compound according to the invention, and instead of one dispersing and/or emulsifying agent, a mixture of such agents.

Mixtures of water-soluble and water-insoluble solvents are usually employed as the solvent addition for the dispersion, the former in most cases predominating. Suitable water-soluble solvents are, for example, mono- or di-alcohols, lower ketones, polyglycol esters and polyglycol ethers or mixtures of such solvents. The solvent component advantageously contains at least one high-boiling, water-soluble solvent, that is to say a solvent with a boiling point above about 150° C. Examples of suitable water-insoluble solvents are esters, ethers and/or higher ketones. Low-boiling solvent portions can be removed again, for example distilled off, at a later point in time if appropriate.

Possible suitable water-soluble high-boiling solvents are, in particular, the ($C_1$–$C_4$)monoalkyl and -dialkyl ethers of diethylene glycol and/or dipropylene glycol. Addition of isopropanol, glycol or glycerol, individually or as a mixture, preferably in an amount of 1 to 5% by weight, based on the final formulation, is furthermore advantageous for the stability of the dispersion. Possible suitable water-insoluble solvents are, above all, butyl esters, in particular butyl acetate.

Particularly advantageous effects on carpets, especially in respect of the dirt repellant action, are also obtained if the aqueous dispersion according to the invention additionally contains at least one dispersed, optionally also fluorine-containing (meth)acrylic acid ester polymer or copolymer in amounts of 5 to 25% by weight, this amount being chosen so that the amount of (meth)acrylic acid ester polymer or copolymer together with the amount of active compound is 15 to 30% by weight. Such (meth)acrylic acid ester polymers or copolymers are advantageously added to the dispersions according to the invention in the form of a separately prepared aqueous dispersion.

The (meth)acrylic acid ester polymers or copolymers usually contain units of esters of acrylic and/or methacrylic acid with $C_1$- to $C_{18}$-alcohols and can be prepared, for example, in a manner which is known per se. Methacrylic ester copolymers are preferred, especially if the monomer mixture used for their preparation contains at least 80% by weight of esters of $C_1$- to $C_4$-alcohols. Copolymers of methyl methacrylate and isobutyl methacrylate are preferred, especially if the methyl ester content predominates in the copolymer. A copolymer prepared from methyl methacrylate and the isobutyl ester in the weight ratio of 3:1 is particularly preferred. The preparation of a methacrylic acid ester copolymer and dispersion thereof is described in Examples 3(b) and 3(c). Other (meth)acrylic acid ester polymers and copolymers can be prepared and dispersed analogously.

The (meth)acrylic acid ester polymer or copolymer is dispersed cationically if it is added to a cationic dispersion of the methylolated and optionally etherified active compounds according to the invention, and it is dispersed anionically if it is added to an anionic dispersion of the active compounds according to the invention.

Suitable cationic dispersing and/or emulsifying agents for the preparation of the aqueous cationic dispersions according to the invention or for the dispersion of the (meth)acrylic acid ester polymer are, for example, commercially available technical grade products of the formulae 37 to 41.

$$(R_f\!-\!CF\!=\!CH\!-\!CH_2\!-\!NR^6R^7)^{\oplus} Z^{\ominus} \qquad (37)$$

$$(R_f\!-\!CF\!=\!CH\!-\!CH_2\!-\!N(CH_3)_2CH_2CH_2OH)^{\oplus} Z^{\ominus} \qquad (38)$$

$$R_f\!-\!CF\!=\!CH\!-\!CH_2\!-\!NR^8\!-\!CH_2CH_2OH)^{\oplus} Z^{\ominus} \qquad (39)$$

wherein $R_f'$ denotes a perfluoroalkyl radical with 4 to 15 C atoms, preferably 6 to 12 C atoms, $R^6$ and $R^7$ denote —$CH_3$, —$C_2H_5$, —$C_3H_7$ or —$C_4H_9$, $Z^{\ominus}$ denotes $SO_4CH_3$ or Cl and $R^8$ denotes —H or —$CH_3$. Such cationic dispersing and/or emulsifying agents, like the anionic dispersing and/or emulsifying agents still to be mentioned, can also be used in combination with nonionic dispersing and/or emulsifying agents. Nonionic products which are suitable for such a combination are, for example, polyoxyethylene derivatives of sorbitan anhydrides which are partly esterified with fatty acid, such as, for example, polyoxyethylene sorbitan monooleate, and furthermore polyoxyethylene derivatives of fatty alcohols or of fluorine alcohols. Suitable polyoxyethylene derivatives of fluorine alcohols have the formula 40

$$R_f'\!-\!CH_2CH_2\!-\!(OCH_2CH_2)_u\!-\!OH \qquad (40)$$

wherein u is a number from 4 to 16, preferably 5 to 13, and $R_f'$ has the meaning already given. Such nonionic products are also commercially available.

The anionic aqueous dispersions of the methylolated and optionally etherified active compounds according to the invention are preferred. To prepare these anionic aqueous dispersions or the anionically dispersed (meth)acrylic acid polymer or copolymer, preferably at least one emulsifier of the formula 41

$$R_f'\!-\!CH_2CH_2O\!-\!CO\!-\!NH\!-\!CH_2CH_2\!-\!SSO_3X^2 \qquad (41)$$

wherein $R_f'$ has the meaning already given and $X^2$ denotes a monovalent cation, is used in combination with at least one nonionic emulsifier of the formula 42

$$R_f'\!-\!CH_2CH_2\!-\!(OCH_2CH_2)_v\!-\!OH \qquad (42)$$

wherein $R_f'$ has the meaning already given and v denotes a number from 0 to 10.

If several compounds with $R_f'$ radicals are used, for example those of the formulae 34 to 42, the $R_f'$ radicals do not have to be identical.

The compounds of the formula 34 to 42 can be used in the form of their commercially available technical grade mixtures, which as a rule contain several compounds of the type mentioned with various perfluoroalkyl radicals $R_f'$.

The monovalent cation $X^2$ in the compounds of the formula 41 is as a rule an alkali metal cation, in particular the sodium or potassium cation or the ammonium cation. If appropriate, the ammonium cation can also be substituted by organic radicals, for example it can be triethanolammonium.

In the commercially available mixtures of the emulsifiers of the formula 40, v is, in particular, about 6.

The methylolated and optionally etherified compounds of the formula 1 according to the invention can be converted into an aqueous dispersion, in particular an anionic aqueous dispersion, more easily than the non-methylolated starting compounds of the formula 1.

In the form of their solutions in organic solvents and preferably in the form of their aqueous dispersions, the active compounds according to the invention are suitable for the treatment of textiles of natural or synthetic fibres, in particular of polyamide, polyester, polyacrylonitrile and wool, or mixtures of these types of fibre, and for leather. The textile material can be in any desired form, thus, for example, as thread, fibre, yarn, flocks, woven fabric, knitted fabric or non-woven fabric, but in particular as carpet. The active compounds according to the invention can be used for the treatment either by themselves or in combination with other treatment agents, such as textile resins based on glyoxal or derivatives thereof, plasticizers, PVA and EVA or similar dispersions.

The aqueous dispersions according to the invention meet all the requirements of practice and in particular have an outstanding long-term stability at temperatures from $-20°$ to $+40°$ C. Although they freeze at minus temperatures, the dispersion remains after thawing, in contrast to the previously known dispersions. The aqueous, in particular anionic dispersions according to the invention show an outstanding oleophobic, hydrophobic, dirt repellant and conductivity-improving effect in textile treatment. The adhesion of the active compounds to the substrate is also good during washing or cleaning operations.

The active compounds according to the invention can be applied to the textile material or leather in the form of their solutions in organic solvents or, preferably, in the form of their aqueous dispersions. The solutions or dispersions can thereby be used in the form in which they are obtained during preparation. Usually, however, they will be diluted with water to a solids content of 1 to 10% by weight, preferably 1.5 to 5% by weight, for use. They can be applied in any suitable manner to the textile material to be treated, thus, for example, by spraying, nippadding, padding and the like. Repetition of the process can promote penetration of the substrate and increase the effectiveness of the active compound. The amount applied is chosen so that usually 0.01 to 1% by weight, preferably 0.05 to 0.2% by weight, of fluorine is present on the material. This approximately corresponds to an amount of 0.1 to 10, preferably 0.5 to 4% by weight solids content. After application to the material to be treated, the material is dried at temperatures up to about 120° C., for example at 100° to 120° C., and heat treatment is then carried out at temperatures of about 130° to 200° C., depending on the nature of the substrate, preferably at 140° to 180° C., and usually lasts about 4 minutes to about 30 seconds. The drying and heat treatment can be carried out in different devices or in the same device.

It seems as if the high-boiling organic solvents preferably contained in the dispersion also have an important significance in the fixing of the active compound on the fibre in the sense of a type of carrier effect.

The starting compounds of the formula 1 are known in some cases. The starting compounds of the formula 1 which are known and those which have not yet been described can be prepared by reaction of a fluoroalkanol of the formula 1 b

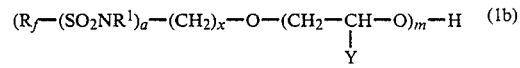

with an isocyanate of the formula 43

wherein $R_f$, $R^1$, Y, a, x, m, p and R have the meanings already given. The reaction is usually carried out in a molar ratio of (1 b):(43)=p:1. However, it can also be carried out with less than the equivalent amount of compound 1 b, in particular in a molar ratio of (1 b):(43)=(p−1):1 if one (or if appropriate also several) isocyanate group(s) present in the polyisocyanate of the formula 45 is (are) to be converted into one or more substituents other than 1a by subsequent reaction, for example with an alcohol, a CH-acid or NH-acid compound.

In the reaction of the isocyanate of the formula 43 with less than the equivalent amount of a fluoroalkanol of the formula 1 b, the adduct of the formula 44

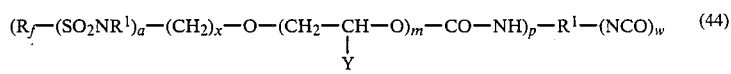

is first formed and is then reacted with another fluoroalkanol of the formula 1 b or a CH-acid or NH-acid compound or a compound of the formula 45

wherein $R^3$ has the meaning already given above, or with water.

Fluoroalkanols of the formula 1 b are commercially available where m=0. Fluoroalkanols of the formula 1 b where m=1, 2, 3 or 4 can be prepared by reacting a perfluoroalkanol of the following formula 46

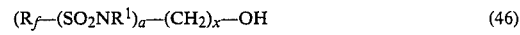

wherein $R_f$, $R^1$, a and x have the meanings already given, or a mixture of such perfluoroalkylethanols with epichlorohydrin, for the introduction of Y=—CH$_2$Cl, or with ethylene oxide, for the introduction of Y=H, or with propylene oxide, for the introduction of Y=—CH$_3$, in the presence of Lewis acids as the catalyst at a temperature of 50° to 150° C., preferably 70° to 90° C., in an appropriate molar ratio.

The perfluoroalkanol of the formula 46 as a rule consists of inexpensive commercially available mixtures with various perfluoroalkyl radicals $R_f$ in which $R_f$ on average has 9 to 13 C atoms. The nature of the Lewis acid is not critical. BF$_3$, boron trifluoride-diethyl etherate, SnCl$_4$, SbCl$_5$, TiCl$_4$, FeCl$_3$, PF$_3$ and/or dibutyltin dilaurate are preferred, boron trifluoridediethyl etherate being particularly preferred. The amount of catalyst is in general 0.01 to 5% by weight, preferably 0.1 to 1% by weight, based on the perfluoroalkanol. The reaction is preferably carried out with stirring and under the pressure which is established, and the liquid epichlorohydrin preferably used (boiling point under normal conditions 116° C.) is added to the alcohol initially taken. The duration of the reaction is in the range from about 0.5 to 7 hours. It may be advantageous to use a solvent. Preferred solvents are halogenated hydrocarbons, such as carbon tetrachloride, trichloroethylene, 1,2-dichloroethane, trichloroethane, pentafluoromonochloroethane and trifluorodichloroethane; ketones, such as methyl ethyl ketone and cyclohexanone; ethers, such as diisopropyl ether and tetrahydrofuran; dimethylformamide and N-methylpyrrolidone.

The reaction between the compound 46 and the epichlorohydrin preferably used proceeds quantitatively. The solvent which is used if appropriate is distilled off from the reaction product obtained, any volatile constituents present, such as unreacted epichlorohydrin, also being removed. For reasons of expediency, the distillation can also be carried out in vacuo (waterpump vacuum). The Lewis acid which is used as the catalyst and does not in itself interfere in the subsequent reaction with the isocyanate can be washed out or neutralized with the aid of alkaline agents, preferably with the aid of an aqueous sodium bicarbonate solution or an amine, such as triethylamine.

The reaction to prepare the starting compounds of the formula 1 is as a rule carried out such that the compounds 1 b or the mixture of compounds 1 b is melted and the isocyanate of the formula 43 or the mixture of isocyanates of the formula 43 is then added dropwise at a temperature about 5° to 10° C. above the boiling point, with stirring. The mixture is then heated up to temperatures of about 130° C. in the course of about one hour, the reaction proceeding slightly exothermically from a temperature of about 80° C. Finally, the reaction is brought to conclusion by a reaction time of about three hours at 130° C. The progress of the reaction can be checked continuously by IR spectroscopy for the disappearance of the isocyanate bands on samples taken. If the reaction has still not come to conclusion within the stated time, the reaction time must be prolonged, for example to 6 hours.

To introduce the radical 29 and 29a, tolylene diisocyanate, in particular tolylene 2,4- and/or 2,6-diisocyanate, is used, in particular in the form of a commercial product which contains about 80% by weight of tolylene 2,4-diisocyanate and about 20% by weight of tolylene 2,6-diisocyanate.

To prepare starting compounds of the formula 1 in which R denotes a mixture of the formulae 30 and 32, industrially obtainable "biuret triisocyanate" of the formula 47

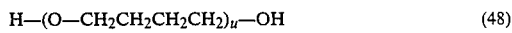

$$OCN-(CH_2)_q-N-CO-NH-(CH_2)_q-NCO \quad (47)$$
$$\phantom{OCN-(CH_2)_q-N}|$$
$$\phantom{OCN-(CH_2)_q-}CO$$
$$\phantom{OCN-(CH_2)_q-N}|$$
$$OCN-(CH_2)_q-NH$$

wherein q has the meaning already given and preferably denotes 6, is used, for example, as the isocyanate of the formula 43 and is reacted with 2 mol of the fluoroalkanol of the formula 1 b and with 1 mol of a compound of the formula 48

$$H-(O-CH_2CH_2CH_2CH_2)_u-OH \quad (48)$$

Starting compounds of the formula 1 where R is a radical of the formula 31 can be prepared by reaction of 1 mol of "biuret triisocyanate" with 2 mol of fluoroalkanol of the formula 1 b and simultaneous or subsequent reaction with 0.5 mol of water.

The preparation of typical starting compounds of the formula 1 is also described in the following examples. Other starting compounds of the formula 1 can be prepared analogously in the general sense.

In the following examples, temperatures are stated in degrees Celsius and, unless indicated otherwise, percentage data denote percentages by weight. Furthermore, in the examples:
1. Desmodur ® N 75 = a technical grade mixture of "biuret triisocyanate" of the formula 47 wherein q denotes 6, approximately 75% strength in ethylglycol acetate/xylene (1:1), from BAYER AG.
2. "Perfluorooctylethanol" = a technical grade mixture of various perfluoroalkylethanols of the formula $$R_F-CH_2CH_2OH \quad (49)$$

wherein the radical $R_F$ consists of $C_8F_{17}$ radicals to the extent of 50 to 55%, of $C_{10}F_{21}$ radicals to the extent of 25 to 30% and of $C_{12}F_{25}$ radicals or perfluoroalkyl radicals with more than 12 C atoms to the extent of 10 to 15%, and the difference to make up to 100% consists of $C_6F_{13}$ radicals. The average molecular weight is 534.
3. Tween ® 80 = polyoxyethylene sorbitan monooleate with a total of about 20 oxyethylene groups. (The tradename is registered for ICI America Inc.)
4. DABCO = 1,4-diazabicyclo(2.2.2)-octane (= triethylenediamine)

EXAMPLE 1

Monomethylolation of 2,4(2,6)-bis(2-perfluoroalkylethoxycarbonylamino)-toluene (a) Preparation of the starting substance 2,4(2,6)-bis(2-perfluoroalkylethoxycarbonylamino)-toluene of the formula 50:

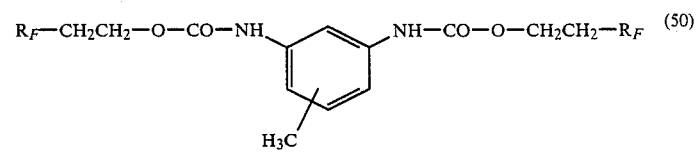

wherein $R_F$ denotes perfluoroalkyl with 8 to 12 C atoms: 1,080 g (=2 mol) of a commercially available mixture of 2-perfluoroalkyl-ethanols of the formula 51

$$R_F-CH_2CH_2-OH \quad (51)$$

which contains individual products with perfluoroalkyl radicals with 8 to 12 C atoms, are heated up to above the melting point of 65° C. in a reaction vessel. 174.16 g (=1 mol) of a technical grade mixture of 80% of tolylene 2,4- and 20% of tolylene 2,6-diisocyanate are then added dropwise in the course of 30 minutes at a temperature of 70° to 75° C., with stirring. The mixture is then heated up to 130° C. in the course of 1 hour, the reaction proceeding slightly exothermically from 80° C., and the temperature is kept at 130° C. for about 3 hours.

The progress of the reaction is checked by IR spectroscopy for the disappearance of the isocyanate bands on samples taken. If appropriate, the reaction time is shortened or lengthened.

1,154 g of a yellowish melt which solidifies to a crystalline cake on cooling are obtained. Melting point: 116° to 120° C. Average fluorine content: 60.5%.

(b) Monomethylolation of the product obtained above according to (a), a product of the formula 50 according to the invention but in which one hydrogen on an —NH group is replaced by —CH$_2$OH being obtained:

615 g (0.5 mol) of 2,4-bis-(2-perfluoroalkylethoxycarbonylamino)-toluene of the formula 50, 260 g of diethylene glycol dimethyl ether as the solvent and 0.5 g of triethylenediamine (="DABCO") as the catalyst are stirred at 60°-65° C. in a 2 l fournecked flask with ground joints and with a stirrer, thermometer and reflux condenser. 35 g (0.525 mol) of a 45% strength solution of formaldehyde in isobutanol are then allowed to run in and the mixture is subsequently stirred at 60°-65° C. for 8 hours. A 910 g yield of a pale homogeneous solution which solidifies to a yellowish paste on cooling is obtained. Free formaldehyde is virtually no longer detectable.

EXAMPLE 2

Preparation of the bismethylol compound of the formula 52

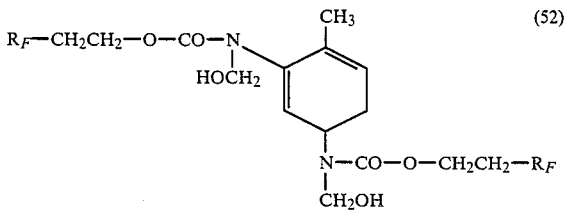
(52)

in the form of a mixture with perfluoroalkyl radicals R$_F$ with 8 to 12 C atoms:

The product mixture of the formula 50 obtained according to Example 1(a) is reacted in accordance with Example 1(b). However, instead of triethylenediamine, 2.5 g of N,N-dimethylethanolamine are used as the basic catalyst and twice the amount (=70 g) of the 45% strength solution of formaldehyde in isobutanol (=1.05 ml) is used. Yield: 947.5 g of a pale paste.

EXAMPLE 3

(a) Preparation of an anionic aqueous dispersion according to the invention of the methylolation product according to Example 2:

13.7 g of the product prepared according to Example 2, 5 g of diethylene glycol dimethyl ether, 5 g of dipropylene glycol monomethyl ether and 3 g of technical grade perfluoroalkylethylpolyglycol of the formula 53

(53)

are dissolved at 70° to 80° C. in a 200 ml three-necked flask with ground glass joints and a beaker shape. 5 g of 25% strength isopropanolic solution of a commercially available emulsifier of the formula 54

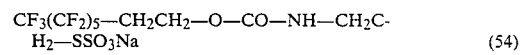
(54)

are then mixed in at 70° C.

A solution of 1.25 g of the compound of the formula 54 in 48.75 ml of water is added dropwise to the solution at 70° C. in the course of 2 to 3 minutes, under application of the powerful shearing forces of a dispersing machine of the Ultraturrax type, the temperature dropping to 45° to 50° C. The dispersion process is continued at this temperature for a further 10 to 15 minutes. A crude dispersion which is outwardly appropriate but is not yet storage-stable in this form and soon settles is thereby already formed.

The resulting crude dispersion is then subjected to subsequent fine treatment, and in particular by sonic treatment by means of an ultrasonic machine (for example of the Sonifier type from Branson), until 90% of the particles have reached or fallen below an average size of 1 µm. This usually takes 10 to 15 minutes. The temperature is thereby initially kept at 40° to 45° C. by cooling with water, and towards the end is reduced to 20° to 30° C. by cooling with ice-water.

20 g of the approximately 40% strength anionically dispersed methacrylic ester copolymer according to the following Example (b) are then added to this fine dispersion thus obtained. The entire formulation is then treated with ultrasound again for about 2 minutes at 20° to 30° C., with cooling. 100 g of a fine, milky-opaque dispersion which has a fluorine content of 7% (based on the active substance) and is also very stable to storage at temperatures from −20° C. to +45° C. are obtained.

After cooling to −20° C. for 24 hours, no change in the dispersion was to be observed on thawing again.

(b) Preparation of a methacrylic acid ester copolymer.

75 g of methyl methacrylate and 25 g of isobutyl methacrylate are taken in a 250 ml reservoir vessel equipped with a stirrer and bottom discharge and are stirred to give a homogeneous solution, after which the stirrer is stopped.

130 g of water, 30 g of a 25% strength isopropanolic solution of a commercially available emulsifier of the formula 54 and 22 ml of the monomer solution from the reservoir vessel are taken in a 500 ml polymerization flask equipped with a stirrer, thermometer, gas inlet tube, reflux condenser, dropping funnel and feed possibility from the reservoir vessel. The polymerization flask is heated up to 50° C. by means of an electrically heated waterbath (55° C. bath), while stirring and passing in a weak stream of nitrogen into the solution. When this temperature is reached, 0.2 g of potassium persulphate is added in one portion. The polymerization reaction will start immediately thereafter, and can be detected by a rise in temperature to about 57° C. and a change in colour (bluish fluorescence). When the internal temperature exceeds 56° C., dropwise addition of the monomer solution from the reservoir vessel and of a separately prepared catalyst solution consisting of 0.2 g of sodium pyrosulphite (Na$_2$S$_2$O$_5$) and 10 g of water is started. At the same time, the introduction of nitrogen can be discontinued. The monomer solution should be metered in after about 1 hour and the catalyst solution somewhat later.

During this entire dropwise addition phase, the reaction temperature is 55° to 60° C. with an unchanged bath temperature of 55° C. When the dropwise addition has ended, the polymer emulsion is initially heated to 60° to 62° C. (65° C. bath temperature) and is subsequently stirred under these conditions for 1 hour, and is then cooled to room temperature and filtered over a PE sieve bag (105 μm). 270.4 g of an approximately 40% strength whitish, opaque dispersion are obtained. (c) Preparation of a methacrylic acid ester copolymer.

The procedure is as in the preceding Example (b), but the 30 g of the isopropanolic solution of the emulsifier used therein are replaced by 4 g of a commercially available alkanesulphonate used as a detergent base (for example the commercial product ®Warolat U from Bayer AG).

244.2 g of an approximately 40% strength whitish, opaque dispersion are obtained.

EXAMPLE 4

Monomethylolation of a product mixture of the formula 55

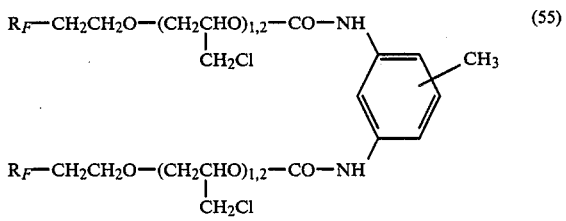

where $R_F$ = perfluoroalkyl with 6 to 14 C atoms:

(a) Preparation of the starting substance of the formula 55:

548.5 g (0.84 mol) of perfluoroalkylethanol-epichlorohydrin adduct according to the following Example (b) are taken in molten form at 80° C. in a 1 liter flask with a stirrer, condenser with a drying tube, thermometer and heating bath. 73.1 g (=0.42 mol) of a technical grade mixture of 80% of tolylene 2,4- and 20% of tolylene 2,6-diisocyanate are added dropwise, with stirring. The mixture is then subsequently stirred at 110° C. for 5 hours. Yield: 614 g (=98.8% of theory) of a solid waxy yellow-coloured product of the formula 55 (molecular weight in practice=1610) with a fluorine content of 51.4%.

(b) Preparation of the perfluoroalkylethanol-epichlorohydrin adduct of the formula 56

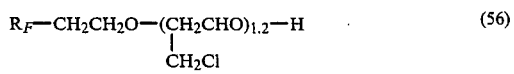

where $R_F$ = perfluoroalkyl with 6 to 14 C atoms:

1.5 kg (2.78 mol) of a commercially available perfluoroalkylethanol mixture $R_FCH_2CH_2OH$ (perfluoroalkyl $R_F=C_6F_{13}$ to $C_{14}F_{29}$; OH number=104), 450 ml of 1,2,2-trifluorotrichloroethane ($CFCl_2$-$CF_2Cl$; boiling point=48° C.) as the solvent and 15 g of boron trifluoride-diethyl etherate as the catalyst (that is to say 1% by weight of catalyst, based on the perfluoroalkylethanol) are taken in a 2 l flask with a stirrer, reflux condenser, thermometer, dropping funnel and heating bath. 309 g (3.34 mol) of epichlorohydrin are added dropwise to this solution at 50° C. (with cooling), after which the mixture is subsequently stirred at the boiling point of the solvent for 2 hours. The contents of the flask of the catalyst are now washed with 1 l of a 4% strength by weight aqueous sodium bicarbonate solution and then rinsed twice with water and distilled under a waterpump vacuum to remove the solvent.

The resulting perfluoroalkylethanol-epichlorohydrin adduct (1.77 kg; yield: 97.6% by weight of theory) is a solid (waxy) yellow-coloured product (OH number 85.9); its empirical composition corresponds to the formula 56.

(c) Monomethylolation 81 g (=0.05 mol) of the starting substance of the formula 55 prepared according to the above Example (a), 19 g of diethylene glycol dimethyl ether as the solvent, 0.2 g of triethylamine as the catalyst and 3.4 g of a 45% strength (about 0.05 mol) solution of formaldehyde in isobutanol are stirred at 55° to 60° C. for 6 hours. The yield obtained is 103 g of a brownish, viscous solution of the monomethylol product of the formula 57, one hydrogen on an —NH group being replaced by —CH$_2$OH, containing 82.2% of active substance (of molecular weight in practice of 1,640).

EXAMPLE 5

(a) Preparation of a cationic dispersion according to the invention:

23.2 g of substance mixture according to Example 4(b) (containing 17.6 g of monomethylolated active compound, dissolved essentially in diethylene glycol dimethyl ether), 1 g of additional diethylene glycol dimethyl ether, 10 g of dibutyl adipate, 5 g of methylpropylene glycol acetate and 2 g of Tween ®80 are dissolved at 60°–70° C. A solution of 1.4 g of the compound 57

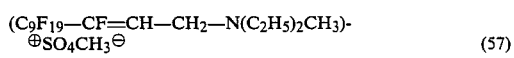

in 57.4 g of water are then allowed to run in, with stirring, and the mixture is treated with ultrasound at 70°–75° C. for 10 to 20 minutes until the average particle size has fallen below 1 μm. 100 g of a stable whitish emulsion with a fluorine content of 7.2% in the active substance are obtained.

This dispersion is suitable above all for the treatment of polyamide carpets, which are then subjected to the thermosol process at 150° C. for 3 minutes.

EXAMPLE 6

Methylolation with subsequent etherification 81 g (=0.05 mol) of the starting substance of the formula 55 prepared according to Example 4(a), 19 g of diethylene glycol dimethyl ether, 0.3 g of lauryldimethylamine as the catalyst and 3.8 g of a 40% strength solution of formaldehyde in isobutanol are stirred at 55°–60° C. for 2 hours. 50 ml of methanol and 0.4 g of orthophosphoric acid are then added and heating is continued at 55°–60° C. for 4 hours. Finally, the excess methanol is distilled off under a waterpump vacuum. 113 g of a viscous product coloured somewhat redbrown are obtained.

EXAMPLE 7

Bismethylolation of a product mixture of $$HO(CH_2CH_2CH_2CH_2O)_{8.5}CONH(CH_2)_6NH \qquad (58)$$
$$\begin{array}{cc} | & | \\ CH_2Cl & CO \\ | & | \\ R_FCH_2CH_2O(CH_2CHO)_2CONH(CH_2)_6N \\ & | \\ & CO \\ & | \\ R_FCH_2CH_2O(CH_2CHO)_2CONH(CH_2)_6NH \\ | \\ CH_2Cl \end{array}$$

and $$\begin{array}{c} CH_2Cl \\ | \\ R_FCH_2CH_2O(CH_2CHO)_2CONH(CH_2)_6NH \\ | \\ CO \\ | \\ HO(CH_2CH_2CH_2CH_2O)_{8.5}CONH(CH_2)_6N \\ | \\ CO \\ | \\ R_FCH_2CH_2O(CH_2CH)_2CONH(CH_2)_6NH \\ | \\ CH_2Cl \end{array} \qquad (59)$$

with $R_F$=perfluoroalkyl with 6 to 14 C atoms, obtainable by reaction of 1 mol of Desmodur N 75 with about 2 mol of a compound of the formula 66

$$R_FCH_2CH_2O(CH_2CHO)_2H \qquad (66)$$
$$\phantom{R_FCH_2CH_2O(CH_2C}|$$
$$\phantom{R_FCH_2CH_2O(CH_2C}CH_2Cl$$

(compare Example 13(a) and 1 mol of polybutylene glycol of the formula 59a $$HO(CH_2CH_2CH_2CH_2O)_{8.5}H \qquad (59a).$$

129.6 g (=0.05 mol) of the product mixture, 32.4 g of dibutyl adipate, 0.2 g of DABCO and 7.4 g of a 45% strength solution of formaldehyde in isobutanol are heated at 55° to 60° C. for 4 hours, with stirring. A 169.6 g yield of crude bismethylol compound is obtained in the form of an amber-coloured viscous solution.

EXAMPLE 8

Preparation of a cationic dispersion according to the invention 30 g of the viscous solution obtained according to Example 7, 5 g of diethylene glycol dimethyl ether, 5 g of methoxypropyl acetate and 3 g of Tween®80 are dissolved, with heating. A solution of 3 g of a 50% strength solution of $$(R_F-CF=CH-CH_2-N(CH_3)_3)^{\oplus}Cl^{\ominus} \qquad (60)$$

where $R_F$ is perfluoroalkyl with 6 to 14 C atoms, in isopropanol, dissolved in 54 g of water, are then allowed to run in, with stirring, and the mixture is treated sonically at 70° to 75° C. intensively for 12 minutes. 100 g of a very attractive white emulsion with a content of 5% of fluorine in the active substance are obtained.

EXAMPLE 9

Finishing of polyamide woven fabric with an emulsion according to Example 8

2 g of the emulsion according to Example 8 are diluted with 98 g of water. A standardized polyamide woven fabric is then soaked with this solution and squeezed off on a padder (squeeze-off effect 50%). The fabric is then dried at 120° C. for 3 hours and finally subjected to the thermosol process at 200° C. for 30 seconds.

The oleophobicity test according to AATCC carried out after the thermosol treatment gives a rating of 6 to 7 and thus shows an effectiveness improved by half the rating in comparison with a non-methylolated comparison product.

EXAMPLE 10

Etherification of the bismethylol compound of Example 7

3.5 g of paraformaldehyde (0.11 mol) are first largely predissolved in an excess of 40 ml of methanol at 50° C. for 10 minutes. 129.6 g (0.05 mol) of the reaction product obtained according to Example 7, 32.4 g of dibutyl adipate and 0.5 g of $$CF_3-(CF_2)_5-CH_2-CH_2-O-CO-CH_2-CH_2-N\begin{array}{c}C_4H_9\\ \diagdown \\ C_4H_9\end{array} \qquad (61)$$

(the latter as the catalyst) are then added and the mixture is heated at 55° C. for 2 hours. It is then rendered acid with 0.2 ml of concentrated HCl and heating is continued at 55° to 60° C. for 3 hours. Finally, the excess methanol is distilled off at about 50° C. under a slight vacuum. A 170 g yield of amber-coloured viscous product (with a content of 5% of fluorine in the active substance) is obtained.

EXAMPLE 11

Preparation of a cationic dispersion according to the invention 23.2 g of the solvent-containing fluorine product according to Example 10 are dissolved with 7.5 g of dibutyl adipate, 5 g of diethylene glycol dimethyl ether, 5 g of butylglycol acetate and 3 g of an addition product of 100 EO (ethylene oxide units) on nonylphenol and 0.75 g of the compound of the formula 62 at $$(R_FC_2H_4O(CH_2CHO)_2CONHC_6H_{12}NHCO)_2NC_6H_{12}NHCO(OC_2H_4)_{22.9}OCH_3 \qquad (62)$$
$$\phantom{(R_FC_2H_4O(CH_2C}|$$
$$\phantom{(R_FC_2H_4O(CH_2C}CH_2Cl$$

100° C. A solution of 2.15 g of a 70% strength solution of the compound $$R_F-CF-CH-CH_2N^{\oplus}(CH_3)_3 \; Cl^{\ominus} \qquad (60a)$$

$$R_F-C_6F_{13}-C_{16}F_{33}$$

in isopropanol, dissolved in 54.1 g of water, are then allowed to run in, with thorough stirring, and the mixture is subsequently treated sonically at 75° to 80° C. for 12 minutes until an average particle size of 1 μm or preferably somewhat lower is reached. A very attractive whitish emulsion which remains stable for months.

EXAMPLE 12

Bismethylolation during simultaneous dispersion (a) Preparation of the starting compound:

355 g of "perfluorooctylethanol" (=0.66 mol) are dissolved with 150 g of diethylene glycol dimethyl ether at 50° C. in a 2 l four-necked flask with a ground joint and with a stirrer, dropping funnel and condenser. 0.5 ml of dibutyltin dilaurate as the catalyst is then added, and 204 g of Desmodur N 75 (=0.33 mol) are added dropwise in the course of half an hour, with stirring. The temperature in the flask rises to about 70° C. as a result of the exothermic reaction. The mixture is heated at 100° C. for a further 2 hours, the solution is then allowed to cool to 60° C. and 18 g of water (=1 mol=500% excess) are subsequently added dropwise, with thorough stirring. The carbon dioxide formed in the urea formation escapes with moderate evolution of gas. The mixture is subsequently stirred at 100° C. until practically all the isocyanate has been consumed (about 1 to 2 hours).

Yield=722 g of a pale 79% strength solution with an F content of 35%, which solidifies to a gel on cooling.

The product has the formula 63

$$R_FCH_2CH_2-O-CONH-(CH_2)_6-N-CO-NH-(CH_2)_6-NH \atop \underset{R_FCH_2CH_2-O-CONH-(CH_2)_6-NH}{\overset{CO}{|}} \quad (63)$$

$$\underset{R_FCH_2CH_2-O-CONH-(CH_2)_6-N-CO-NH-(CH_2)_6-NH}{\overset{CO}{\underset{|}{R_FCH_2CH_2-O-CONH-(CH_2)_6-NH}}}$$

wherein $R_F$ has the meaning given under 2. before the examples.

(b) Bismethylolation and simultaneous dispersion:

56.25 g of a 40% strength solution of an emulsifier of the formula 64

$$(R_fCF=CHCH_2N(C_2H_5)_2CH_3)^{\oplus}SO_4CH_3^{\ominus} \quad (64)$$

in the form of a technical grade mixture with an F content of 50% are dissolved in 784 g of water in a 2 l connection piece. A warm solution of 300 g (=0.07 mol) of the 79% strength product according to the above Example (a) and 45 g of Tween ®80 in 300 g of butyl acetate, at 80° C., is then allowed to run in, under the powerful shearing action of a dispersing machine of the Ultraturrax type, in the course of about 10 minutes, during which the temperature in the connection piece rises to about 45° C. The dispersion process is continued at this temperature for a further 10 minutes. The crude dispersion thereby formed is not yet stable on storage.

5 g of paraformaldehyde are now stirred in and the crude dispersion is treated in circulation with ultrasound or in a high pressure homogenizer until the average degree of distribution of the particles has fallen below an average diameter of 1 μm. The methylolation has then also ended, since free formaldehyde can no longer be detected.

1,500 g of a stable 14.3% strength whitish dispersion with a fluorine content of 7% and a solids content of 20.2% are obtained.

(c) Bismethylolation and simultaneous dispersion:

In the Example (b) described above, the paraformaldehyde used can advantageously be replaced by 12 g of a 40% strength solution of formaldehyde in isobutanol.

EXAMPLE 13

Tetramethylolation and etherification of the product of the formula $$\underset{R_FCH_2CH_2OCONH-(CH_2)_6NHCO}{\overset{R_FCH_2CH_2O(CH_2CHO)_2CONH(CH_2)_6NHCO}{\underset{CH_2Cl}{|}}} \quad \underset{N-(CH_2)_6-NH-CO}{\overset{|}{\underset{O}{|}}} \quad (65)$$

$$\underset{R_FCH_2CH_2OCONH-(CH_2)_6NHCO}{\overset{R_FCH_2CH_2O(CH_2CHO)_2CONH(CH_2)_6NHCO}{\underset{CH_2Cl}{|}}} \quad \underset{N-(CH_2)_6-NH-CO}{\overset{|}{\underset{|}{|}}}$$

wherein $R_F$ is a perfluoroalkyl mixture of $C_8F_{17}$ to $C_{17}F_{35}$.

(a) Preparation of the starting substance of the formula 65:

(a 1) 0.8 kg (1.57 mol) of a commercially available perfluoroalkyl ethanol mixture with perfluoroalkyl=$C_8F_{17}$ to $C_{16}F_{33}$ (OH number=106), 0.8 kg of 1,2,2-trifluorotrichloroethane (CFCl$_2$-CF$_2$Cl; boiling point=48° C.) as the solvent and 5 g of boron trifluoride-diethyl etherate as the catalyst (that is to say 0.6% by weight of catalyst, based on perfluoroalkylethanol) are taken in a glass flask equipped with a stirrer, reflux condenser, thermometer, dropping funnel and heating bath. 0.29 kg (3.14 mol) of epichlorohydrin are added dropwise to this solution at 45° C., after which the mixture is kept at the boiling point of the solvent for 3 hours. The solvent used is then distilled off under a waterpump vacuum. A waxy yellow-coloured product is present. The molar ratio of perfluoroalkylethanol to epichlorohydrin in the aliphatic perfluoroalkylethanol thus obtained is 1:2 (m in formula 1 b has the value 2, which results by taking the mean of 1 to 8 epichlorohydrin units added on). The perfluoroalkylethanol prepared therefore has on average the following composition:

$$R_F-CH_2-CH_2-O-(CH_2-\underset{CH_2Cl}{\overset{|}{CH}}-O)_2H \quad (66)$$

(a 2) 162.0 g (0.32 equivalent) of the perfluoroalkylethanol mixture used in (a 1), of the formula 67

$$R_F-CH_2-CH_2OH \quad (67),$$

216.0 g (0.32 equivalent) of the perfluoroalkylethanol of the formula 66

$$R_F-CH_2-CH_2-O-(CH_2-\underset{CH_2Cl}{\overset{|}{CH}}-O)_2H \quad (66)$$

wherein $R_F$ in each case is a perfluoroalkyl mixture of $C_8F_{17}$ to $C_{16}F_{33}$, and 181.3 g (0.96 equivalent) of the triisocyanate of the formula 68

$$\text{OCN—(CH}_2\text{)}_6\text{—NH—CO}\diagdown \atop \text{OCN—(CH}_2\text{)}_6\text{—NH—CO}\diagup \text{N—(CH}_2\text{)}_6\text{—NCO} \quad (68)$$

are taken in a glass flask equipped with a stirrer, reflux condenser with a drying tube, thermometer and heating bath.

The triisocyanate of the formula 68 is thereby used in the form of a mixture obtainable as a commercial product, which moreover also contains the isocyanates $$\text{OCN—(CH}_2\text{)}_6\text{—NH—CO—NH—(CH}_2\text{)}_6\text{—NCO} \quad (69)$$

$$\text{OCN—(CH}_2\text{)}_6\text{—NH—CO—NH—(CH}_2\text{)}_6\text{—N-H—CO—NH—(CH}_2\text{)}_6\text{—NCO} \quad (70)$$

and which contains the triisocyanate of the formula 68 as the main product.

The mixture of products taken (molar ratio 1:1:1) is kept at 110° C. for 5 hours, with stirring. A waxy yellow-coloured product of the following composition is obtained:

$$\begin{array}{c} R_fCH_2CH_2O(CH_2CHO)_2CONH(CH_2)_6NHCO \\ | \qquad\qquad\qquad | \\ CH_2Cl \qquad\qquad N(CH_2)_6\text{—NCO} \\ | \\ R_fCH_2CH_2OCONH(CH_2)_6NHCO \end{array} \quad (71)$$

(a 3) 559.0 g (0.32 equivalent) of the compound 71, 17.5 g (0.32 equivalent) of hydroquinone and 144.0 g of di-n-butyl adipate as the solvent (that is to say a molar ratio of 2:1) are taken in a glass flask equipped with a stirrer, reflux condenser and drying tube, thermometer and heating bath, and the mixture is kept at 110° C. for 10 hours, with stirring. 715.0 g, that is to say 99.2% by weight of theory, of the compound of the formula 65 are obtained in the form of a waxy, brown-coloured product.

(b) Tetramethylolation of the compound 65 and subsequent etherification with methanol:

3.5 g (=0.117 mol) of paraformaldehyde, 40 g of methanol, 30 g of diethylene glycol dimethyl ether, 73 g (0.02 mol) of the compound according to the above Example (a 3) and 5 g of N,N-dimethylethanolamine as the catalyst are heated at 60° to 65° C. for 3 hours. The paraformaldehyde thereby gradually dissolves completely. 0.5 g of orthophosphoric acid is then added and the mixture is heated at 60° to 65° C. for a further 2 hours. The excess methanol is then distilled off under a slight vacuum. 110 g of crude amber-coloured tetramethylol ether (dissolved in diethylene glycol dimethyl ether) are obtained.

EXAMPLE 14

Preparation of a dispersion according to the invention 18.6 g of the solvent-containing product according to Example 13 (b), 10 g of dibutyl adipate, 5 g of methoxypropyl acetate and 2.75 g of the nonionic coemulsifier of the formula $$(R_fC_2H_4O(CH_2CHO)_2CONHC_6H_{12}NHCO)_2NC_6H_{12}NHCO(OC_4H_8)_{23}OCH_3 \quad (72)$$
$$| \atop CH_2Cl$$

are dissolved at 90° to 100° C. A solution of 3 g of a 50% strength solution of $$(R_f\text{—CF}=\text{CH—CH}_2\text{—N(CH}_3)_3)^{\oplus}\text{Cl}^{\ominus} \quad (73)$$

($R_f$ in formulas 72 and 73 each means a mixture of $C_6F_{13}$ to $C_{16}F_{33}$) in isopropanol, dissolved in 60.65 g of water, are then allowed to run in, with stirring, and the mixture is subjected to sonic treatment intensively with ultrasound at 70° to 75° C. for 12 minutes. 100 g of a very attractive whitish emulsion with a content of 5% of fluorine in the active substance are obtained.

EXAMPLE 15

(Comparison Example)

If the product obtained according to Example 12(a) is dispersed without methylolation and etherification according to Example 13, only a distinctly less stable dispersion which already starts to settle after standing at room temperature for 1 to 2 days is obtained.

What is claimed is:

1. Methylolated urethane containing fluoroalkyl ligands prepared by methylolation of a urethane reactant of the formula $$(R_f\text{—(SO}_2NR^1)_a(CH_2)_x\text{—O—(CH}_2\text{—CH—O)}_m\text{—CO—NH)}_p\text{—R} \atop | \atop Y$$

with formaldehyde in a molar ratio of 0.5 to (1.1)t moles urethane reactant per mole formaldehyde wherein $R_f$ denotes perfluoroalkyl with 4 to 20 carbon atoms;
$R^1$ denotes hydrogen or an alkyl with 1 to 4 carbon atoms;
a denotes the number 0 to 1;
x denotes a number from 1 to 4;
Y denotes hydrogen, —CH$_3$ or —CH$_2$Cl;
R denotes $+\text{CH}_2\!\!\rightarrow_q$, $+\text{CH}_2\!\!\rightarrow_q\!\text{O}\!\!\leftarrow\!\!\text{CH}_2\!\!\rightarrow_q$, $+\text{CH}_2\!\!\rightarrow_q\!\text{NH}\!\!\leftarrow\!\!\text{CH}_2\!\!\rightarrow_q$,

[benzene ring structures with CH$_3$ and CH$_2$ substituents]

-continued
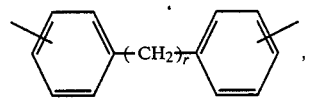
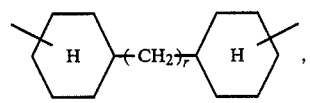
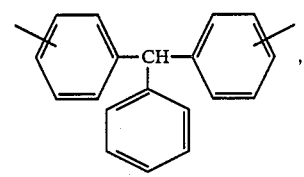
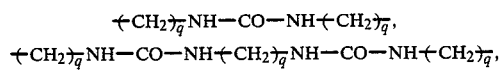
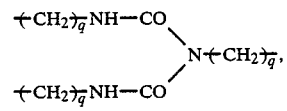
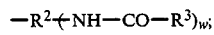
p denotes a number from 1 to 4;
q denotes a number from 2 to 10;
r denotes a number from 1 to 6;
m denotes a number from 0 to 4;
w denotes a number from 1 to 2, with the proviso that the sum of p+w is not more than 3;
$R^2$ denotes a (p+w)-valent radical selected from the group .
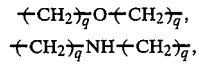
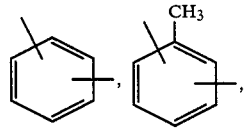
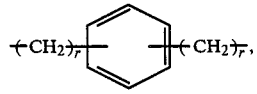
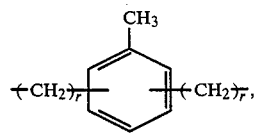
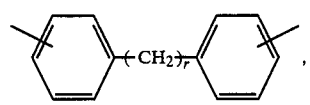
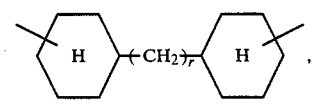
-continued
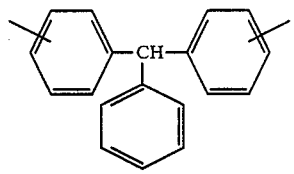
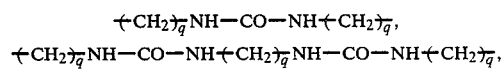
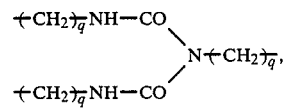
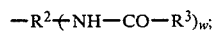
$R^3$ denotes
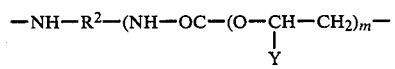
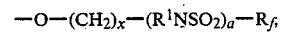
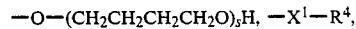
or the radical of a CH-acid or NH-acid compound;
s denotes a number from 1 to 15,
$X^1$ denotes
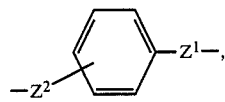
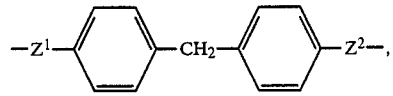
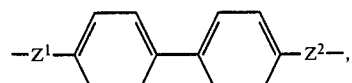
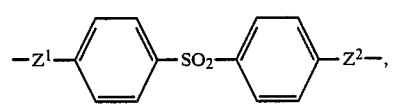
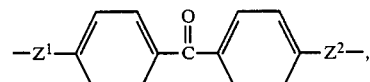
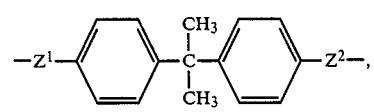
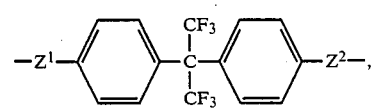

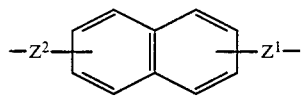

whereby all $X^1$ radicals can be mono- or polysubstituted by alkyl groups with 1 to 4 C atoms;

$Z^1$, $Z^2$ which are identical or different denote —O— or —NH—;

$R^4$ denotes the hydrogen atom, an alkyl group with 1 to 4 C atoms or the group

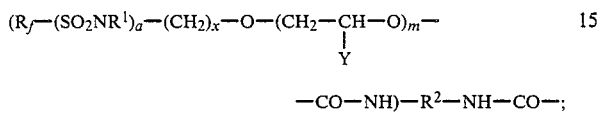

and t is the total number of methylolatable —NH groups in the urethane reactant.

2. Urethanes according to claim 1 which are additionally etherified with an alkanol with 1 to 4 carbon atoms or ethylene glycol monoalkyl ether having 1 to 4 carbon atoms in the alkyl moiety.

3. Urethanes according to claim 1 prepared by reacting 0.5 to (t−1) moles urethane reactant per mole of formaldehyde.

4. Urethanes according to claim 1 prepared by reacting 0.5 to (0.525)t moles urethane reactant per mole of formaldehyde.

5. Urethanes according to claim 1 wherein the methylolation reaction is carried out at temperatures of 20° to 70° C.

6. Process for the preparation of methylolated urethane containing fluoroalkyl ligands which comprises reacting a urethane reactant of the formula

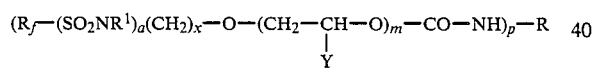

with formaldehyde in a molar ratio of 0.5 to (1.1)t moles urethane reactant per mole of formaldehyde at temperatures from 20° to 70° C. wherein $R_f$ denotes perfluoroalkyl with 4 to 20 carbon atoms;
$R^1$ denotes hydrogen or an alkyl with 1 to 4 carbon atoms;
a denotes the number 0 or 1;
x denotes a number from 1 to 4;
Y denotes hydrogen, —CH$_3$ or —CH$_2$Cl;
R denotes

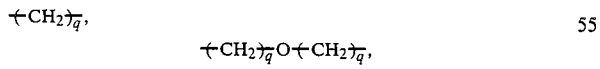

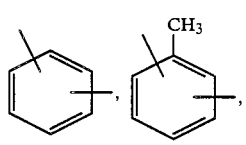

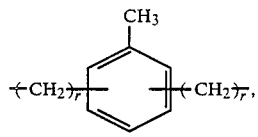

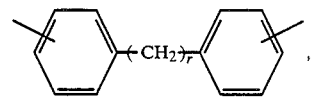

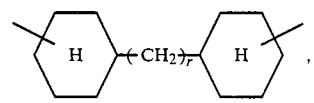

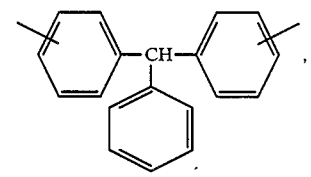

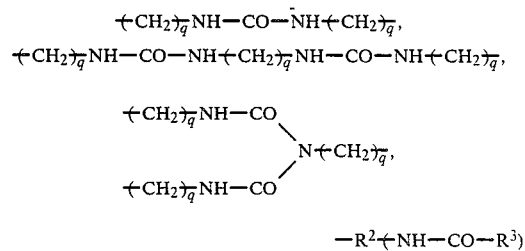

p denotes a number from 1 to 4;
q denotes a number from 2 to 10;
r denotes a number from 1 to 6;
m denotes a number from 0 to 4;
w denotes a number from 1 to 2, with the proviso that the sum of p+w is not more than 3;
$R^2$ denotes a (p+w)-valent radical selected from the group

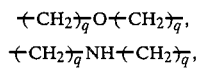

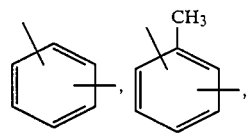

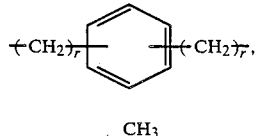

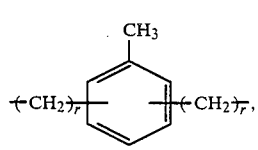

-continued

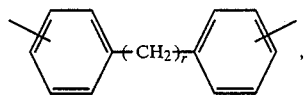

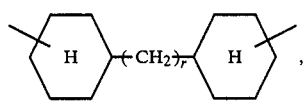

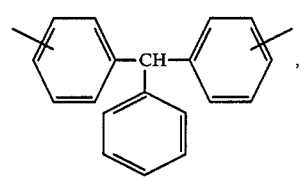

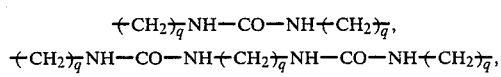

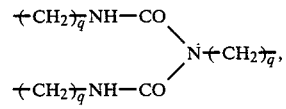

$R^3$ denotes

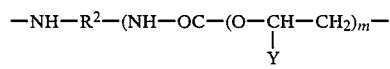

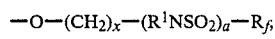

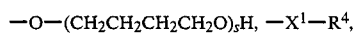

or the radical of a CH-acid or NH-acid compound;
s denotes a number from 1 to 15,
$X^1$ denotes

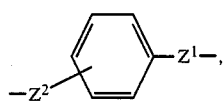

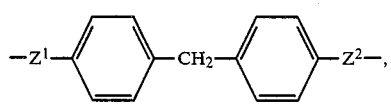

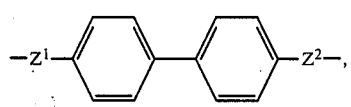

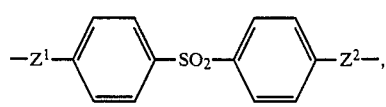

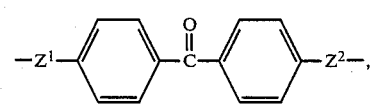

-continued

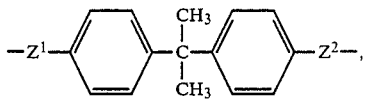

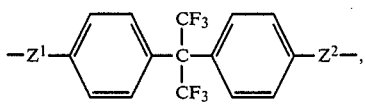

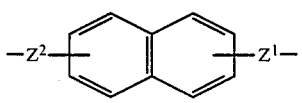

whereby all $X^1$ radicals can be mono- or polysubstituted by alkyl groups with 1 to 4 C atoms;
$Z^1$, $Z^2$ which are identical or different denote —O— or —NH—;
$R^4$ denotes the hydrogen atom, an alkyl group with 1 to 4 C atoms or the group

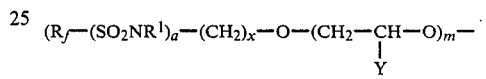

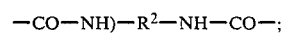

and t is the total number of methylolatable —NH groups in the urethane reactant.

7. Process according to claim 6 wherein the reaction temperature is 30° to 65° C.

8. Process according to claim 6 which further comprises a subsequent etherification with an alkanol with 1 to 4 carbon atoms or ethylene glycol monoalkyl ether having 1 to 4 carbon atoms in the alkyl moiety.

9. Process according to claim 6 wherein 0.5 to (t−1) moles of urethane reactant per mole of formaldehyde reacted.

10. Process according to claim 6 wherein 0.5 to (0.525)t moles of urethane reactant per mole of formaldehyde are reacted.

11. Process according to claim 6 wherein the methylolation reaction is carried out in an organic solvent.

12. Process according to claim 6 wherein the methylolation reaction is carried out in the presence of a basic catalyst.

13. Aqueous dispersion of methylolated urethanes containing fluoroalkyl ligands containing
   5 to 30% by weight of methylolated urethanes according to claim 1,
   2 to 15% by weight of one or more dispersing or emulsifying agents,
   5 to 30% by weight of solvent comprising mono- or dialcohols, ketones, esters, ethers, polyglycol esters, polyglycol ethers, ($C_1$-$C_4$)monoalkyl and -dialkyl ethers of diethyleneglycol and/or dipropyleneglycol, glycol or a mixture thereof, and water as the remainder to make up to 100%.

14. A method for hydrophobic or oleophobic finishing textiles or leather which comprises applying to textiles or leather a solution or aqueous dispersion of methylolated urethanes according to claim 1.

15. Textiles and leathers hydrophobically or oleophobically finished by the method of claim 14.

* * * * *